United States Patent
Thurmond et al.

(10) Patent No.: US 6,784,288 B2
(45) Date of Patent: Aug. 31, 2004

(54) POLYNUCLEOTIDE AND POLYPEPTIDE SEQUENCES OF MONKEY CATHEPSIN S

(75) Inventors: Robin Thurmond, San Diego, CA (US); Lars Karlsson, La Jolla, CA (US); Sherry Baker, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 234 days.

(21) Appl. No.: 10/010,577

(22) Filed: Nov. 8, 2001

(65) Prior Publication Data

US 2003/0104971 A1 Jun. 5, 2003

(51) Int. Cl.[7] .......................... C12N 15/57; C12N 9/64; C12N 15/74; C12N 15/79; C12Q 1/37

(52) U.S. Cl. ...................... 536/23.2; 435/23; 435/69.1; 435/226; 435/252.3; 435/320.1

(58) Field of Search ..................... 536/23.2; 435/69.1, 435/226, 23, 252.3, 320.1

(56) References Cited

U.S. PATENT DOCUMENTS

| | | | |
|---|---|---|---|
| 4,568,649 A | 2/1986 | Bertoglio-Matte | 436/534 |
| 5,776,718 A | 7/1998 | Palmer et al. | 435/23 |
| 5,976,858 A | 11/1999 | Palmer et al. | 435/219 |
| 6,030,946 A | 2/2000 | Klaus et al. | 514/12 |
| 6,369,032 B1 * | 4/2002 | Gu et al. | 514/12 |
| 6,579,896 B2 * | 6/2003 | Cai et al. | 514/406 |
| 6,583,155 B2 * | 6/2003 | Butler et al. | 514/300 |
| 2002/0055497 A1 * | 5/2002 | Butler et al. | 514/210.2 |
| 2003/0073672 A1 * | 4/2003 | Breitenbucher et al. | 514/151 |

FOREIGN PATENT DOCUMENTS

| | | |
|---|---|---|
| WO | WO 99/24460 | 5/1999 |
| WO | WO 99/58153 | 11/1999 |
| WO | WO 9963115 | 12/1999 |
| WO | WO 02/21129 A1 * | 3/2002 |

OTHER PUBLICATIONS

Baker et al., "Cloning, Expression, Purification, And Activity Of Dogs (*Canis familiaris*) And Monkey (*Saimiri boliviensis*) cathepsin S", *Protein Expression Purification*, vol. 28, pp. 93–101, 2003.

McQueney et al., "Cynomolgus Monkey (*Macaca fascicularis*) Cathepsin K: Cloning, Expression, Purification, And Activation", *Protein Expression Purification*, vol. 14, pp. 387–394, 1998.

Peppard et al., "Effect Of Selective And Non–Selective Cysteine Protease Inhibitors On The Intracellular Processing Of Interleukin 6 By HEPG2 Cells", *In Vitro Cellular & Developmental Biology–Animal*, vol. 35, pp. 459–464, 1999.

Schneider et al., "Human Cathepsin S Nucleotide Sequence", EBI Database Accession No. AAZ56150, Mar. 27, 2000.

Altschul et al., "Basic Local Alignment Search Tool", *J. Molec. Biol.* (1990) 215(3):403–410.

Bellon et al., "Purification and Biochemical Characterization of Recombinant Hirudin Produced by *Saccharomyces cerevisiae*", *Biochem.* (1989) 28:2941–2949.

(List continued on next page.)

Primary Examiner—Nashaat Nashed
Assistant Examiner—William W. Moore

(57) ABSTRACT

DNAs encoding monkey cathepsin S have been cloned and characterized. The recombinant protein is capable of forming biologically active protein. The cDNA's have been expressed in recombinant host cells that produce active recombinant protein. The recombinant protein is also purified from the recombinant host cells. In addition, the recombinant host cells are utilized to establish a method for identifying modulators of the receptor activity, and receptor modulators are identified.

8 Claims, 5 Drawing Sheets

```
  1 atgaagcagc tggtttgtgt gctgtttgtg tgctcctctg cggtgacaca gttgcataaa
 61 gatcccaccc tggatcacca ctggaatctc tggaagaaaa cctacggcaa acaatataaa
121 gaaaagaatg aagaagcagt acgacgtctc atctgggaga agaatctaaa gtttgtgatg
181 cttcacaacc tggagcattc aatgggaatg cactcatatg atctgggcat gaaccacctg
241 ggagacatga ccagtgaaga agtgatgtct ttgatgagtt ccctgagagt tcccaaccag
301 tggcagagaa atatcacata taagtcaaac cctaatcaga tgttgcctga ttctgtggac
361 tggagagaaa agggggtgtgt taccgaagtg aaatatcaag gttcttgtgg tgcttgctgg
421 gctttcagtg ctgtggggc octggaagca cagctgaagc tgaaaacagg aaagctggtg
481 tctctcagtg cccagaacct ggtggattgc tctgaaaaat atggaaacaa aggttgcaat
541 ggtggcttca tgacagaggc tttccagtac atcattgata acaaaggcat tgactcagaa
601 gcttcctatc cctacaaagc cacggatcag aaatgtcagt atgactcaaa atatcgtgct
661 gccacatgtt caaagtacac tgaacttccg tatggcagag aagatgtcct gaaagaagct
721 gtggccaata aaggcccagt gtgtgttgga gtagatgcaa gtcatccttc cttcttcctc
781 tacagaagtg gtgtctacta tgacccagcc tgtactcaga aggtgaatca tggtgtactt
841 gtgattggct atggtgacct taatgggaaa gaatactggc ttgtgaaaaa cagctgggc
901 agcaacttttg gtgaacaagg atatattcgg atggcaagaa ataaaggaaa ccactgtggg
961 attgctagtt acccctctta cccagaaatc tag
```

OTHER PUBLICATIONS

Dieter Brömme and Mary E. McGrath, "High Level Expression and Crystallization of Recombinant Human Cathepsin S", *Protein Science* (1996) 5(4):789–791.

Brömme et al., "Functional Expression of Human Cathepsin S in *Saccharomyces cerevisiae*: Purification and Characterization of the Recombinant Enzyme", *J. Biol. Chem.* (Mar. 5, 1993) 268(7):4832–4838.

M. Buroker–Kilgore and K. K. Wang, "A Coomassie Brilliant Blue G–250–Based Colorimetric Assay for Measuring Activity of Calpain and Other Proteases", Anal. Biochem. (1993) 208:387–392.

H. Carillo and D. Lipman, "The Multiple Sequence Alignment Problem in Biology", *SIAM J. Applied Math.* (1988) 48(5):1073–1082.

Coolican et al., "The Role of Subunit Autolysis in Activation of Smooth Muscle Ca2+– Dependent Proteases", *J. Biol. Chem.* (1986) 261(9):4170–4176.

Devereux et al., "A Comprehensive Set of Sequence Analysis Programs for the VAX", *Nucleic Acids Research* (1984) 12(1, Pt. 1):387–395.

Ecker et al., "Increasing Gene Expression in Yeast by Fusion to Ubiquitin", *J. Biol. Chem.* (1989) 264(13):7715–7719.

Horowitz et al., "Synthesis and Assembly of Fuctional Mammalian Na,K–ATPase in Yeast", *J. Biol. Chem.* (1990) 265(8):4189–4192.

Jacobson et al., "Expression and Secretion of Biologically Active Echistatin in *Saccharomyces cerevisiae*", *Gene* (1989) 85(2):511–516.

Randall J. Kaufman and Phillip A. Sharp, "Amplification and Expression of Sequences Cotransfected with a Modular Dihydrofolate Reductase Complementary DNA Gene", *J. Mol. Biol.* (1982) 159:601–621.

Heidrun Kirshcke, "Cathepsin S", *Handbook of Proteolytic Enzymes*, (A. J. Barret, N. D. Rawlings, and J. F. Woessner (Eds.)) San Diego: Academic Press (1998) Chapter 211:621–624.

Kirschke et al., "Cathepsin S: The Cystein Proteinase from Bovine Lymphoid Tissue is Distinct From Cathepsin L (E.C. 3.4.22.15)" *Biochem. J.* (1986) 240(2):455–459.

G. Kohler and C. Milstein, "Continuous Cultures of Fused Cells Secreting Antibody of Predefined Specificity", *Nature* (1975) 256:495–497.

Kopitar et al., "Folding and Activation of Human ProCathepsin S from Inclusion Bodies Produced in *Escherichia coli*", *Eur. J. Biochem.* (1996) 236(2):558–562.

Lonergan et al., "Improved Calpain Assay Using Fluorescein Isothiocyanate–Labeled Casein", J. Food Sci., (1995) 60(1):72–73.

McDonnell et al., "Reconstitution of the Vitamin D–Responsive Osteocalcin Transcription Unit in *Saccharomyces cerevisiae*", *Mol. Cell. Biol.* (1989) 9(8):3517–3523.

Nakagawa et al., "Impaired Invariant Chain Degradation and Antigen Presentation and Diminished Collagen–Induced Arthritis in Cathepsin S Null Mice", *Immunity*(1999) 10(2):207–217.

M. Ng and D. S. Auld, "A Fluorescent Oligopeptide Energy Transfer Assay with Broad Applications for Neutral Proteases", Anal. Biochem. (1989) 183:50–56.

Rattan et al., "Protein Synthesis: Posttranslational Modifications and Aging", *Aging and Cellular Defense Mechanisms, Ann. N.Y. Acad. Sci.* (1992) 663:48–62.

Riese et al., "Essential Role for Cathepsin S in MHC Class II–Associated Invariant Chain Processing and Peptide Loading", *Immunity*, (1996) 4(4):357–366.

Riese et al., "Cathepsin S Activity Regulates Antigen Presentation and Immunity", *J. Clin. Invest.* (1998) 101(11):2351–2363.

Rinas et al., "Characterization of Recombinant Factor XIIIa Produced in *Saccharomyces cerevisia*", *Bio/Technology* (1990) 8(6):543–546.

Sabin et al., "High–Level Expression and In Vivo Processing of Chimeric Ubiquitin Fusion Proteins In *Saccharomyces cerevisiae*", *Bio/Technology* (1989) 7(7):705–709.

Sieckevitz et al., "Activation of the HIV–1 LTR by T Cell Mitogens and the Trans–Activator Protein of HTLV–I", *Science* (1987) 238:1575–1578.

Sam Seifter and Sasha Englard, "Analysis for Protein Modifications and Nonprotein Cofactors", *Methods in Enzymol.* (1990) 182(46: Characterization of Purified Proteins):626–646.

Shi et al., "Cathepsin S Required for Normal MHC Class II Peptide Loading and Germinal Center Development", *Immunity* (1999) 10(2):197–206.

Sleep et al., "The Secretion of Human Serum Albumin from the Yeast *Saccharomyces cerevisiae* Using Five Different Leader Sequences", *Biotechnology* (1990) 8:42–46.

Sally S. Twining, "Fluorescein Isothiocyanate–Labeled Casein Assay for Proteolytic Enzymes", *Anal. Biochem.* (1984) 143:30–34.

Wadstroem and Smyth, "Zymogram Methods Applied to Thin–Layer Isoelectric Focusing in Polyacrylamide Gel", *Sci. Tools* (1973) 20(2–3):17–21.

Finn Wold, "Posttranslational Protein Modifications: Perspectives and Prospects", *Posttranslational Covalent Modification Of Proteins*, (B. C. Johnson, (Ed.) Academic Press, New York, 1983) p. 1–12.

Yamamoto et al., "Important Role of the Proline Residue in the Signal Sequence that Directs the Secretion Of Human Lysozyme In *Saccharomyces cerevisiae*" *Biochemistry* (Mar. 1989) 28(6):2728–2732.

\* cited by examiner

Figure 1

```
  1 atgaagcagc tggtttgtgt gctgtttgtg tgctcctctg cggtgacaca gttgcataaa
 61 gatcccaccc tggatcacca ctggaatctc tggaagaaaa cctacggcaa acaatataaa
121 gaaaagaatg aagaagcagt acgacgtctc atctgggaga agaatctaaa gtttgtgatg
181 cttcacaacc tggagcattc aatgggaatg cactcatatg atctgggcat gaaccacctg
241 ggagacatga ccagtgaaga agtgatgtct ttgatgagtt ccctgagagt tcccaaccag
301 tggcagagaa atatcacata taagtcaaac cctaatcaga tgttgcctga ttctgtggac
361 tggagagaaa agggtgtgt taccgaagtg aaatatcaag gttcttgtgg tgcttgctgg
421 gctttcagtg ctgtgggggc cctggaagca cagctgaagc tgaaaacagg aaagctggtg
481 tctctcagtg cccagaacct ggtggattgc tctgaaaaat atggaaacaa aggttgcaat
541 ggtggcttca tgacagaggc tttccagtac atcattgata acaaaggcat tgactcagaa
601 gcttcctatc cctacaaagc cacggatcag aaatgtcagt atgactcaaa atatcgtgct
661 gccacatgtt caaagtacac tgaacttccg tatggcagag aagatgtcct gaaagaagct
721 gtggccaata aaggcccagt gtgtgttgga gtagatgcaa gtcatccttc cttcttcctc
781 tacagaagtg gtgtctacta tgacccagcc tgtactcaga aggtgaatca tggtgtactt
841 gtgattggct atggtgacct taatgggaaa gaatactggc ttgtgaaaaa cagctggggc
901 agcaactttg gtgaacaagg atatattcgg atggcaagaa ataaaggaaa ccactgtggg
961 attgctagtt accctctta cccagaaatc tag
```

Figure 2

MET LYS GLN LEU VAL CYS VAL LEU PHE VAL CYS SER SER ALA VAL THR GLN
LEU HIS LYS ASP PRO THR LEU ASP HIS HIS TRP ASN LEU TRP LYS LYS THR TYR
GLY LYS GLN TYR LYS GLU LYS ASN GLU GLU ALA VAL ARG ARG LEU ILE TRP
GLU LYS ASN LEU LYS PHE VAL MET LEU HIS ASN LEU GLU HIS SER MET GLY
MET HIS SER TYR ASP LEU GLY MET ASN HIS LEU GLY ASP MET THR SER GLU
GLU VAL MET SER LEU MET SER SER LEU ARG VAL PRO ASN GLN TRP GLN ARG
ASN ILE THR TYR LYS SER ASN PRO ASN GLN MET LEU PRO ASP SER VAL ASP TRP
ARG GLU LYS GLY CYS VAL THR GLU VAL LYS TYR GLN GLY SER CYS GLY ALA
CYS TRP ALA PHE SER ALA VAL GLY ALA LEU GLU ALA GLN LEU LYS LEU LYS
THR GLY LYS LEU VAL SER LEU SER ALA GLN ASN LEU VAL ASP CYS SER GLU
LYS TYR GLY ASN LYS GLY CYS ASN GLY GLY PHE MET THR GLU ALA PHE GLN
TYR ILE ILE ASP ASN LYS GLY ILE ASP SER GLU ALA SER TYR PRO TYR LYS ALA
THR ASP GLN LYS CYS GLN TYR ASP SER LYS TYR ARG ALA ALA THR CYS SER
LYS TYR THR GLU LEU PRO TYR GLY ARG GLU ASP VAL LEU LYS GLU ALA VAL
ALA ASN LYS GLY PRO VAL CYS VAL GLY VAL ASP ALA SER HIS PRO SER PHE
PHE LEU TYR ARG SER GLY VAL TYR TYR ASP PRO ALA CYS THR GLN LYS VAL
ASN HIS GLY VAL LEU VAL ILE GLY TYR GLY ASP LEU ASN GLY LYS GLU TYR TRP
LEU VAL LYS ASN SER TRP GLY SER ASN PHE GLY GLU GLN GLY TYR ILE ARG
MET ALA ARG ASN LYS GLY ASN HIS CYS GLY ILE ALA SER TYR PRO SER TYR
PRO GLU ILE

Panel A

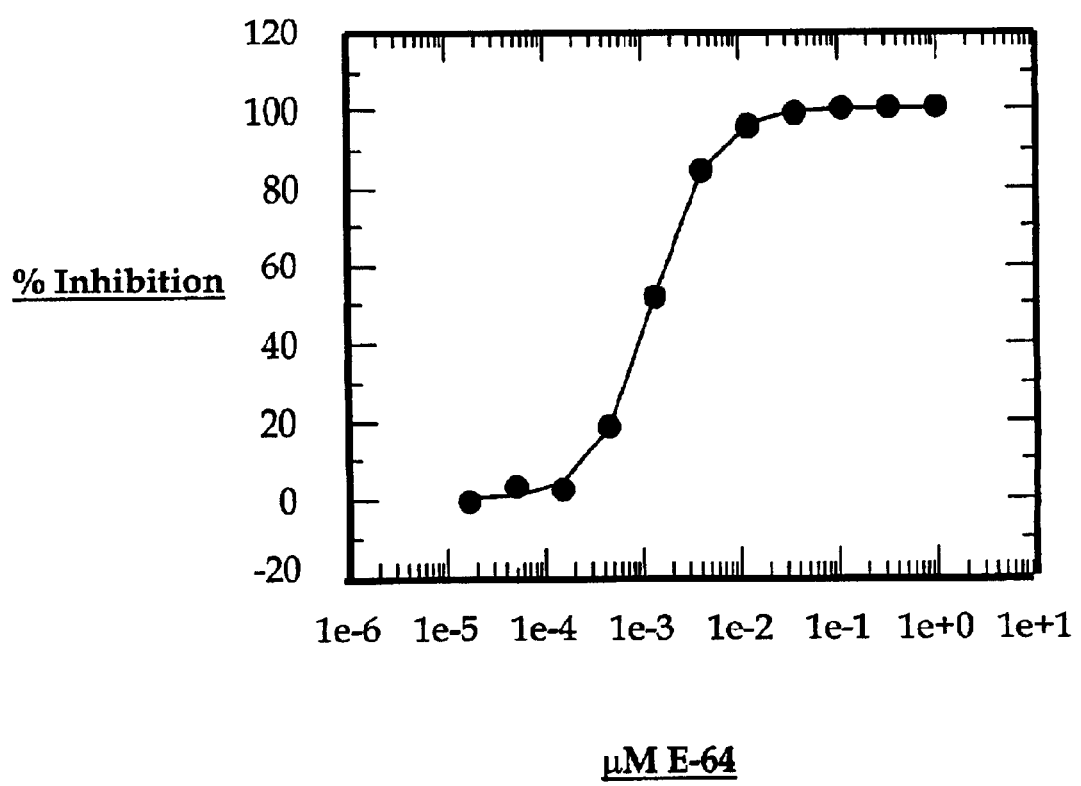

POLYNUCLEOTIDE AND POLYPEPTIDE SEQUENCES OF MONKEY CATHEPSIN S

BACKGROUND OF THE INVENTION

Cathepsin S (EC 3.4.22.27) is a cysteine protease of the papain family found primarily in lysosomes (D. Bromme and M. E. McGrath, "High Level Expression and Crystallization of Recombinant Human Cathepsin S", *Protein Science* (1996) 5:89–791). Cathepsin S (CatS) is a cysteine protease expressed in lymphatic tissues. It is has been identified as playing a major role in invariant chain proteolysis which is a prerequisite for peptide loading of MHC class II (Riese et al., *Immunity* (1996) 4:357). It has 50 to 60% identity to cathepsins L and K, but differs in that it has a broad pH optimum that extends to alkaline pH. Inhibitors have been shown in animal models to modulate antigen presentation and are effective in an asthma model (Riese et al., *J. Clin. Invest.* (1998) 101:2351). Mice deficient in cathepsin S have an impaired ability to present exogenous proteins by professional antigen presenting cells (Nakagawa et al., *Immunity* (1999) 10:207; Shi et al., *Immunity* (1999) 10:197).

The role of cathepsin S in the immune response is anticipated by its tissue distribution: cathepsin S is found primarily in lymphatic tissues, lymph nodes, the spleen, B lymphocytes, and macrophages (H. Kirschke, "Chapter 211: Cathepsin S" in *Handbook of Proteolytic Enzymes*, (A. J. Barrett, N. D. Rawlings, and J. F. Woessner (Eds.)) San Diego:Academic Press (1998) 621–624). Cathepsin S inhibitors have been shown in animal models to modulate antigen presentation and are effective in an animal model of asthma (R. J. Riese, R. N. Mitchell, J. A. Villadangos, G. P. Shi, J. T. Palmer, E. R. Karp, G. T. De Sanctis, H. L. Ploegh, and H. A. Chapman, "Cathepsin S Activity Regulates Antigen Presentation and Immunity", *J. Clin. Invest.* (1998) 101:2351–2363; G. P. Shi, J. A. Villadangos, G. Dranoff, C. Small, L. Gu, K. J. Haley, R. Riese, H. L. Ploegh, and H. A. Chapman, "Cathepsin S Required for Normal MHC Class II Peptide Loading and Germinal Center Development", *Immunity* (1999) 10:197–206).

The recognition of antigen-presenting MHC class II molecules by CD4[+] T cells is a crucial component of the immunological response. Class II molecules, like other transmembrane proteins, are translocated into the endoplasmic reticulum after synthesis, where they associate with a third protein, the invariant chain (Ii). This molecule is a type II transmembrane protein that serves as a class II-specific chaperone which promotes the exit of class II-Ii complexes from the endoplasmic reticulum and prevents class II molecules from binding peptides and unfolded proteins in the endoplasmic reticulum and in the secretory pathway.

A targeting motif in the cytoplasmic tail of Ii directs the complexes from the secretory pathway into the endosomal system. Before the MHC class II molecules can present antigen, the Ii must be removed. This is accomplished by a series of proteases that break Ii down into small peptides. However, an Ii fragment, called class II-associated invariant chain peptide (CLIP), which occupies the peptide-binding groove of the class II molecule, is in most cases not spontaneously released. The CLIP fragment serves as a substitute peptide that protects the class II binding pocket from collapsing both during intracellular transport and after Ii degradation in the endosomal system. Binding of antigenic peptides, generated from endocytosed proteins, requires an empty, yet open binding site, and therefore CLIP has to be released while the open binding site needs to be stabilized to allow the binding of other peptides. Human Leukocyte Antigen DM ('HLA-DM') has been well documented to mediate both of these functions, thus promoting the binding of antigenic peptides. After acquiring peptides, the class II molecules are transported to the cell surface via routes that are largely unknown.

Blocking the presentation of antigens is a promising way to inhibit the immune response. This could be done by disrupting the uptake, the proteolytic processing, or binding to MHC class II molecules. Blocking the uptake may be problematic since many different cell types require this function. Inhibition of the proteolytic processing of particular antigens may be of use since different proteases may be involved in cleaving different antigens, however, these proteases are not specific and may lead to other side effects. One way to specifically block the binding to the antigens to the MHC class II is to inhibit the proteolysis of the invariant chain. If this is not removed, the MHC class II molecules cannot be loaded with peptides, hence blocking Ii degradation would decrease antigen presentation to CD4+ T-cells and disrupt the normal immune response.

Mice in which the gene encoding cathepsin S has been knocked out are less susceptible to collagen-induced arthritis and their immune systems have an impaired ability to respond to antigens (T. Y. Nakagawa, W. H. Brissette, P. D. Lira, R. J. Griffiths, N. Petrushova, J. Stock, J. D. McNeish, S. E. Eastman, E. D. Howard, S. R. M. Clarke, E. F. Rosloniec, E. A. Elliott, and A. Y. Rudensky, "Impaired Invariant Chain Degradation and Antigen Presentation and Diminished Collagen-Induced Arthritis in Cathepsin S Null Mice", *Immunity* (1999) 10:207–217). These data demonstrate that compounds that inhibit the proteolytic activity of human cathepsin S should find utility in the treatment of chronic autoimmune diseases including, but not limited to, lupus, rheumatoid arthritis, and asthma; and have potential utility in modulating the immune response to tissue transplantation.

There are a number of cathepsin S inhibitors reported in the literature, some of which are listed below. Certain dipeptidyl nitriles are claimed by Novartis as cathepsin S inhibitors (Altmann et. al.: WO 99/24460). Dipeptidyl vinyl sulfones are claimed by Arris (now Axys Pharmaceuticals, Inc.) as cysteine protease (including cathepsin S) inhibitors (Palmer et al.: U.S. Pat. No. 5,976,858). Certain peptidyl sulfonamides are claimed by Arris/Axys as cysteine protease (including cathepsin S) inhibitors (Palmer et al.: U.S. Pat. No. 5,776,718 [assigned to Arris, now Axys]; Klaus et al.: U.S. Pat. No. 6,030,946 [assigned to Axys]).

Methods of modulating autoimmunity with an agent that modulates cathepsin S activity, e.g. proteolysis of the Ii chain, as well as methods of treating a subject having an autoimmune disorder, methods of evaluating a treatment for its ability to modulate an immune response are described in WO 99/58153.

SUMMARY OF THE INVENTION

A DNA molecule encoding monkey cathepsin S has been cloned and characterized and it represents a novel nucleotide and amino acid sequence. Using a recombinant expression system functional DNA molecules encoding the monkey cathepsin S protease have been isolated. The biological and structural properties of these proteins are disclosed, as is the amino acid and nucleotide sequence. The recombinant DNA molecules, and portions thereof, are useful for isolating homologues of the DNA molecules, identifying and isolating genomic equivalents of the DNA molecules, and identifying, detecting or isolating mutant forms of the DNA molecules. The recombinant protein is useful to identify modulators of functional cathepsin S. Modulators identified in the assays disclosed herein are useful as therapeutic agents. The monkey cathepsin S nucleic acid and polypeptide molecules of the present invention are also useful in studying the properties of cathepsin S modulators, such as in developing compounds intended for pharmaceutical use in any species, including but not limited to humans.

BRIEF DESCRIPTION OF THE DRAWING

FIG. 1: The nucleotide sequence of monkey cathepsin S is shown.

FIG. 2: The amino acid sequence of monkey cathepsin S is shown.

DETAILED DESCRIPTION

Definitions

Figure 3:
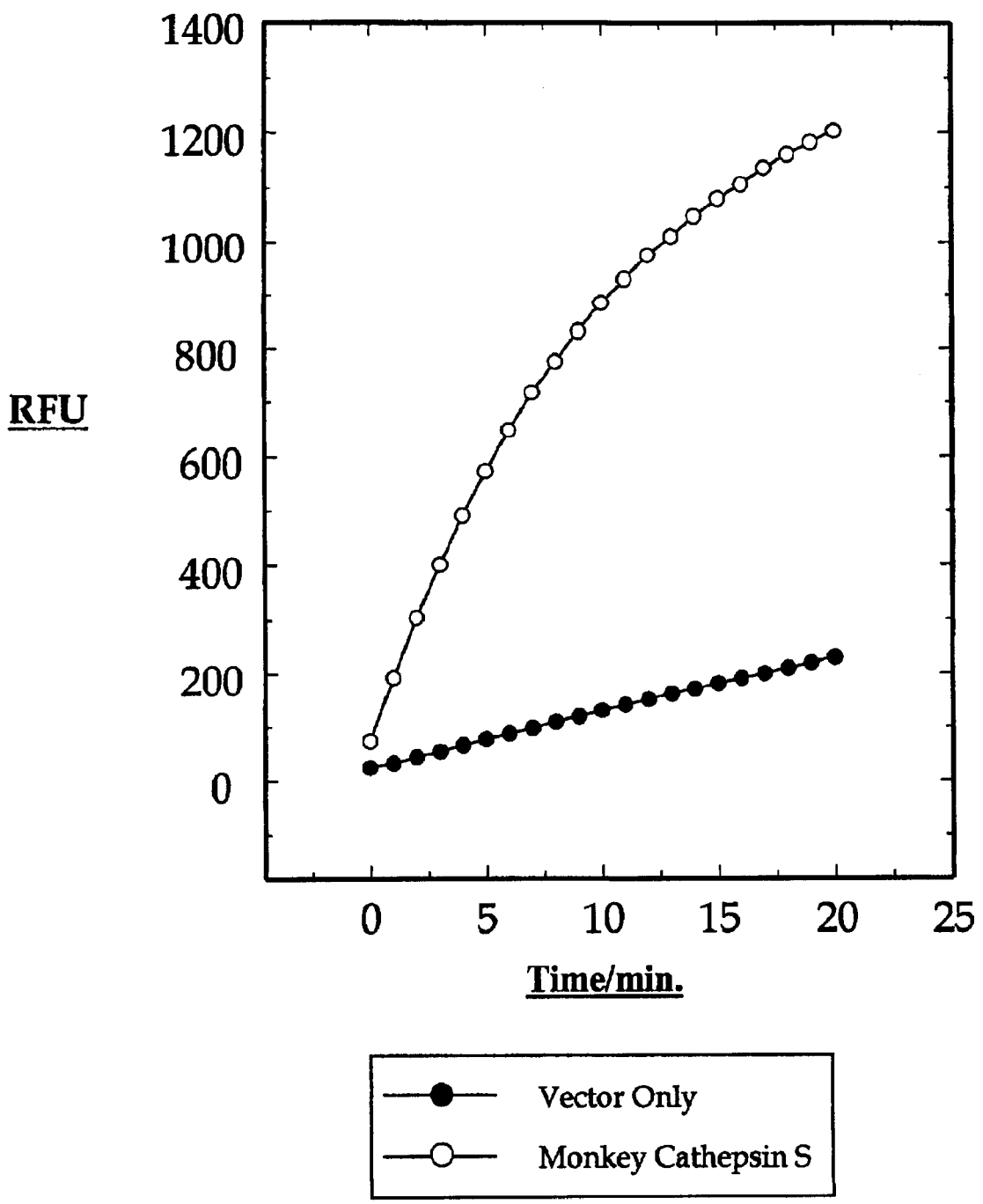
FIG. 3: Functional expression of monkey cathepsin S in recombinant host cells is shown.

The term "protein domain" as used herein refers to a region of a protein that may have a particular three-dimensional structure that may be independent from the remainder of the protein. This structure may maintain a particular activity associated with the domain's function within the protein including enzymatic activity, creation of a recognition motif for another molecule, or provide necessary structural components for a protein to exist in a particular environment. Protein domains are usually evolutionarily conserved regions of proteins, both within a protein family and within protein superfamilies that perform similar functions. The term "protein superfamily" as used herein refers to proteins whose evolutionary relationship may not be entirely established or may be distant by accepted phylogenetic standards, but show a similar three dimensional structure or display unique consensus of critical amino acids. The term "protein family" as used herein refers to proteins whose evolutionary relationship has been established by accepted phylogenic standards.

The term "fusion protein" as used herein refers to protein constructs that are the result of combining multiple protein domains or linker regions for the purpose of gaining the combined functions of the domains or linker regions. This is may be accomplished by molecular cloning of the nucleotide sequences encoding such domains to produce a new polynucleotide sequence that encodes the desired fusion protein. Alternatively, creation of a fusion protein may be accomplished by chemically joining two proteins.

The term "linker region" or "linker domain" or similar such descriptive terms as used herein refers to polynucleotide or polypeptide sequence that are used in the construction of a cloning vector or fusion protein. Functions of a linker region can include introduction of cloning sites into the nucleotide sequence, introduction of a flexible component or space-creating region between two protein domains, or creation of an affinity tag for specific molecule interaction. A linker region may be introduced into a fusion protein resulting from choices made during polypeptide or nucleotide sequence construction.

The term "cloning site" or "polycloning site" as used herein refers to a region of the nucleotide sequence that has one or more available restriction endonuclease consensus cleavage sequences. These nucleotide sequences may be used for a variety of purposes, including but not limited to, introduction into DNA vectors to create novel fusion proteins, or to introduce specific site-directed mutations. It is well known by those of ordinary skill in the art that cloning sites can be engineered at a desired location by silent mutations, conserved mutation, or introduction of a linker region that contains desired restriction enzyme consensus sequences. It is also well known by those of ordinary skill in the art that the precise location of a cloning site can be engineered into any location in a nucleotide sequence.

The term "tag" as used herein refers to an amino acid sequence or a nucleotide sequence that encodes an amino acid sequence that facilitates isolation, purification or detection of a protein containing the tag. A wide variety of such tags are known to those skilled in the art, and are suitable for use in the present invention. Suitable tags include, but are not limited to, HA peptide, polyhistidine peptides, biotin/avidin, and other antibody epitope binding sites.

Isolation of Monkey Cathepsin S Nucleic Acid

The present invention relates to DNA encoding monkey cathepsin S that was isolated from monkey cathepsin S producing cells. Monkey cathepsin S, as used herein, refers to protein that can specifically function as a cysteine protease.

The complete amino acid sequence of monkey cathepsin S was not previously known, nor was the complete nucleotide sequence encoding monkey cathepsin S known. It is predicted that a wide variety of cells and cell types will contain the described monkey cathepsin S. Vertebrate cells capable of producing monkey cathepsin S include, but are not limited to spleen cells, bone marrow cell and other lymphoid cells such as B cells, dendritic cells, and macrophages.

Other cells and cell lines may also be suitable for use to isolate monkey cathepsin S cDNA. Selection of suitable cells may be done by screening for monkey cathepsin S activity in cell extracts or in whole cell assays, described herein. Cells that possess monkey cathepsin S activity in any one of these assays may be suitable for the isolation of monkey cathepsin S DNA or mRNA.

Any of a variety of procedures known in the art may be used to molecularly clone monkey cathepsin S DNA. These methods include, but are not limited to, direct functional expression of the monkey cathepsin S genes following the construction of a monkey cathepsin S-containing cDNA library in an appropriate expression vector system. Another method is to screen monkey cathepsin S-containing cDNA library constructed in a bacteriophage or plasmid shuttle vector with a labeled oligonucleotide probe designed from the amino acid sequence of the monkey cathepsin S subunits. An additional method consists of screening a monkey cathepsin S-containing cDNA library constructed in a bacteriophage or plasmid shuttle vector with a partial cDNA encoding the monkey cathepsin S protein. This partial cDNA is obtained by the specific PCR amplification of monkey cathepsin S DNA fragments through the design of degenerate oligonucleotide primers from the amino acid sequence of the purified monkey cathepsin S protein.

Another method is to isolate RNA from monkey cathepsin S-producing cells and translate the RNA into protein via an in vitro or an in vivo translation system. The translation of the RNA into a peptide a protein will result in the production of at least a portion of the monkey cathepsin S protein which can be identified by, for example, immunological reactivity with an anti-monkey cathepsin S antibody or by biological activity of monkey cathepsin S protein. In this method, pools of RNA isolated from monkey cathepsin S-producing cells can be analyzed for the presence of an RNA that encodes at least a portion of the monkey cathepsin S protein. Further fractionation of the RNA pool can be done to purify the monkey cathepsin S RNA from non-monkey cathepsin S RNA. The peptide or protein produced by this method may be analyzed to provide amino acid sequences which in turn are used to provide primers for production of monkey cathepsin S cDNA, or the RNA used for translation can be analyzed to provide nucleotide sequences encoding monkey cathepsin S and produce probes for this production of monkey cathepsin S cDNA. This method is known in the art and can be found in, for example, T. Maniatis, E. F. Fritsch, and J. Sambrook in *Molecular Cloning: A Laboratory Manual, 2nd Edition*, (1989) Cold Spring Harbor Laboratory Press, Cold Spring Harbor, N.Y.

It is readily apparent to those skilled in the art that other types of libraries, as well as libraries constructed from other cells or cell types, may be useful for isolating monkey cathepsin S-encoding DNA. Other types of libraries include, but are not limited to, cDNA libraries derived from other cells, from organisms other than monkey cathepsin S, and genomic DNA libraries that include YAC (yeast artificial chromosome) and cosmid libraries.

It is readily apparent to those skilled in the art that suitable cDNA libraries may be prepared from cells or cell lines which have monkey cathepsin S activity. The selection of cells or cell lines for use in preparing a cDNA library to isolate monkey cathepsin S cDNA may be done by first measuring cell associated monkey cathepsin S activity using the measurement of monkey cathepsin S-associated biological activity or a ligand binding assay.

Preparation of cDNA libraries can be performed by standard techniques well known in the art. Well known cDNA library construction techniques can be found for example, in T. Maniatis, E. F. Fritsch, and J. Sambrook, *Molecular Cloning: A Laboratory Manual, 2nd Edition* (1989) Cold Spring Harbor Laboratory, Cold Spring Harbor, N.Y.

It is also readily apparent to those skilled in the art that DNA encoding monkey cathepsin S may also be isolated from a suitable genomic DNA library. Construction of genomic DNA libraries can be performed by standard techniques well known in the art. Well known genomic DNA library construction techniques can be found in T. Maniatis, E. F. Fritsch, and J. Sambrook in *Molecular Cloning: A Laboratory Manual, 2nd Edition* (1989) Cold Spring Harbor Laboratory, Cold Spring Harbor, N.Y.

In order to clone the monkey cathepsin S gene by the above methods, the amino acid sequence of monkey cathepsin S may be necessary. To accomplish this, monkey cathepsin S protein may be purified and partial amino acid sequence determined by automated sequenators. It is not necessary to determine the entire amino acid sequence, but the linear sequence of two regions of six to eight amino acids from the protein is determined for the production of primers for PCR amplification of a partial monkey cathepsin S DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the monkey cathepsin S sequence but will be capable of hybridizing to monkey cathepsin S DNA even in the presence of DNA oligonucleotides with mismatches. The mismatched DNA oligonucleotides may still sufficiently hybridize to the monkey cathepsin S DNA to permit identification and isolation of monkey cathepsin S encoding DNA. DNA isolated by these methods can be used to screen DNA libraries from a variety of cell types, from invertebrate and vertebrate sources, and to isolate homologous genes.

Purified biologically active monkey cathepsin S may have several different physical forms. Monkey cathepsin S may exist as a full-length nascent or unprocessed polypeptide, or as partially processed polypeptides or combinations of processed polypeptides. The full-length nascent monkey cathepsin S polypeptide may be posttranslationally modified by specific proteolytic cleavage events that results in the formation of fragments of the full-length nascent polypeptide. A fragment, or physical association of fragments may have the full biological activity associated with monkey cathepsin S however, the degree of monkey cathepsin S activity may vary between individual monkey cathepsin S fragments and physically associated monkey cathepsin S polypeptide fragments.

Because the genetic code is degenerate, more than one codon may be used to encode a particular amino acid, and therefore, the amino acid sequence can be encoded by any of a set of similar DNA oligonucleotides. Only one member of the set will be identical to the monkey cathepsin S sequence but will be capable of hybridizing to monkey cathepsin S DNA even in the presence of DNA oligonucleotides with mismatches under appropriate conditions. Under alternate conditions, the mismatched DNA oligonucleotides may still hybridize to the monkey cathepsin S DNA to permit identification and isolation of monkey cathepsin S encoding DNA.

DNA encoding monkey cathepsin S from a particular organism may be used to isolate and purify homologues of monkey cathepsin S from other organisms. To accomplish this, the first monkey cathepsin S DNA may be mixed with a sample containing DNA encoding homologues of monkey cathepsin S under appropriate hybridization conditions. The hybridized DNA complex may be isolated and the DNA encoding the homologous DNA may be purified therefrom.

Functional Derivatives/Variants

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein, which do not substantially alter the ultimate physical properties of the expressed protein. For example, substitution of aliphatic amino acids alanine, valine, leucine and isoleucine; interchange of the hydroxyl residues serine and threonine, exchange of the acidic residues aspartic acid and glutamic acid, substitution between the amide residues asparagine and glutamine, exchange of the basic residues lysine and arginine and among the aromatic residues phenylalanine, tyrosine may not cause a change in functionality of the polypeptide. Such substitutions are well known and are described, for instance in *Molecular Biology of the Gene, 4th Edition*, Bengamin Cummings Publishing Co. by Watson et al.

It is known that DNA sequences coding for a peptide may be altered so as to code for a peptide having properties that are different than those of the naturally occurring peptide. Methods of altering the DNA sequences include, but are not limited to site directed mutagenesis, chimeric substitution, and gene fusions. Site-directed mutagenesis is used to change one or more DNA residues that may result in a silent mutation, a conservative mutation, or a nonconservative mutation. Chimeric genes are prepared by swapping domains of similar or different genes to replace similar domains in the monkey cathepsin S gene. Similarly, fusion genes may be prepared that add domains to the monkey cathepsin S gene, such as an affinity tag to facilitate identification and isolation of the gene. Fusion genes may be prepared to replace regions of the monkey cathepsin S gene, for example to create a soluble version of the protein by removing a transmembrane domain or adding a targeting sequence to redirect the normal transport of the protein, or adding new post-translational modification sequences to the monkey cathepsin S gene. Examples of altered properties include but are not limited to changes in the affinity of an enzyme for a substrate or a receptor for a ligand. All such changes of the polynucleotide or polypeptide sequences are anticipated as useful variants of the present invention so long as the original function of the polynucleotide or polypeptide sequence of the present invention is maintained as described herein.

Identity or similarity, as known in the art, is relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (*Computational Molecular Biology*, A. M. Lesk, (Ed.), (1988) Oxford University Press, New York; *Biocomputing: Informatics and Genome Projects*, D. W. Smith (Ed.), (1993) Academic Press, New York; *Computer Analysis of Sequence Data, Part* 1, A. M. Griffin and H. G. Griffin (Eds.) (1994) Human Press, New Jersey; *Sequence Analysis in Molecular Biology*, G. von Heinje, (1987) Academic Press; and *Sequence Analysis Primer*, M. Gribskov and J. Devereux, (Eds.) (1991) M. Stockton Press, New York. While there exist a number of methods to measure identity and similarity between two polynucleotide or two polypeptide sequences, both terms are well known to skilled artisans (*Sequence Analysis in Molecular Biology*, G. von Heinje (1987) Academic Press; *Sequence Analysis Primer*, M. Gribskov and J. Devereux (Eds.), (1991) M. Stockton Press, New York; and H. Carillo and D. Lipman, *SIAM J. Applied Math*. (1988) 48:1073). Methods commonly employed to determine identity or similarity between sequences include, but are not limited to those disclosed in H. Carillo and D. Lipman, *SIAM J. Applied Math*. (1988) 48:1073. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux et al. (1984) *Nucleic Acids Research* 12(1):387), BLASTP, BLASTN, and FASTA (Atschul et al. (1990) *J. Molec. Biol.* 215:403).

Polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

The term polypeptide, as used herein, refers to the basic chemical structure of polypeptides that is well known and has been described in textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the twenty amino acids commonly referred to as the twenty naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *Proteins—Structure and Molecular Properties* 2nd Edition, T. E. Creighton, W. H. Freeman and Company, (1993) New York. Many detailed reviews are available on this subject, such as, for example, those provided by F. Wold, "Posttranslational Protein Modifications: Perspectives and Prospects", *Posttranslational Covalent Modification Of Proteins*, (B. C. Johnson, Ed.) (1983) Academic Press, New York; Seifter et al., *Meth. Enzymol.* (1990) 182:626–646; and Rattan et al., "Protein Synthesis: Posttranslational Modifications and Aging", *Ann. N.Y. Acad. Sci.* (1992) 663:48–62. It will be appreciated, as is well known and as noted above, that polypeptides are not always entirely linear. For instance, polypeptides may be generally as a result of posttranslational events, including natural processing event and events brought about by human manipulation that does not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the NH.sub.2-terminus may be deleted. Accordingly, this invention contemplates the use of both the methionine containing and the methionine-less amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell. Variant(s) of polynucleotides or polypeptides, as the term is used herein, are polynucleotides or polypeptides that differ from a reference polynucleotide or polypeptide, respectively. A variant of the polynucleotide may be a naturally occurring variant such as a naturally occurring allelic variant, or it may be a variant that is not known to occur naturally. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of monkey cathepsin S is a compound that possesses a biological activity (either functional or structural) that is substantially similar to the biological activity of monkey cathepsin S. The term "functional derivatives" is intended to include the "fragments," "variants," "degenerate variants," "analogs" and "homologues" or to "chemical derivatives" of monkey cathepsin S. Useful chemical derivatives of polypeptide are well known in the art and include, for example covalent modification of reactive organic site contained within the polypeptide with a secondary chemical moiety. Well-known cross-linking reagents are useful to react to amino, carboxyl, or aldehyde residues to introduce, for example, an affinity tag such as biotin, a fluorescent dye, or to conjugate the polypeptide to a solid phase surface (for example to create an affinity resin). The term "fragment" is meant to refer to any polypeptide subset of monkey cathepsin S. A molecule is "substantially similar" to monkey cathepsin S if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire monkey cathepsin S molecule or to a fragment thereof. Further particularly preferred in this regard are polynucleotides encoding variants, analogs, derivatives and fragments of SEQ ID NO: 1, and variants, analogs and derivatives of the fragments, which have the amino acid sequence of the polypeptide of SEQ ID NO: 2 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the gene of SEQ ID NO: 1. Also especially preferred in this regard are conservative substitutions. Most highly preferred are polynucleotides encoding polypeptides having the amino acid sequence of SEQ ID NO: 2 without substitutions.

Further preferred embodiments of the invention are polynucleotides that are at least 70% identical over their entire length to a polynucleotide encoding the polypeptide having the amino acid sequence set out in SEQ ID NO: 2, and polynucleotides which are complementary to such polynucleotides. Alternatively, highly preferred are polynucleotides that comprise a region that is at least 80% identical, more highly preferred are polynucleotides at comprise a region that is at least 90% identical, and among these preferred polynucleotides, those with at least 95% are especially preferred. Furthermore, those with at least 97% identity are highly preferred among those with at least 95%, and among these those with at least 98% and at least 99% are particularly highly preferred, with at least 99% being the most preferred. The polynucleotides which hybridize to the herein above described polynucleotides in a preferred embodiment encode polypeptides which retain substantially the same biological function or activity as the polypeptide characterized by the deduced amino acid sequence of SEQ ID NO: 2. Preferred embodiments in this respect, moreover, are polynucleotides that encode polypeptides that retain substantially the same biological function or activity as the mature polypeptide encoded by the DNA of SEQ ID NO: 1. The present invention further relates to polynucleotides that hybridize to the herein above described sequences. In this regard, the present invention especially relates to polynucleotides that hybridize under stringent conditions to the herein above described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention may be used as a hybridization probe for RNA, cDNA and genomic DNA to isolate full-length cDNAs and genomic clones encoding the sequences of SEQ ID NO: 1, and to isolate cDNA and genomic clones of other genes that have a high sequence similarity to SEQ ID NO: 1. Such probes generally will comprise at least fifteen bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of SEQ ID NO: 2 (in particular the mature polypeptide) as well as polypeptides which have at least 70% identity to the polypeptide of SEQ ID NO: 2, preferably at least 80% identity to the polypeptide of SEQ ID NO: 2, and more preferably at least 90% similarity (more preferably at least 90% identity) to the polypeptide of SEQ ID NO: 2 and still more preferably at least 95% similarity (still more preferably at least 97% identity) to the polypeptide of SEQ ID NO: 2 and also include portions of such polypeptides with such portion of the polypeptide generally containing at least 30 amino acids and more preferably at least 50 amino acids. Representative examples of polypeptide fragments of the present invention, include, for example, truncation polypeptides of SEQ ID NO: 2. Truncation polypeptides include polypeptides having the amino acid sequence of SEQ ID NO: 2, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Also preferred in this aspect of the invention are fragments characterized by structural or functional attributes of the polypeptide characterized by the sequences of SEQ ID NO: 2. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity or an improved activity, or with a decreased undesirable activity.

Recombinant Expression of Monkey Cathepsin S

The cloned monkey cathepsin S DNA obtained through the methods described herein may be recombinantly expressed by molecular cloning into an expression vector containing a suitable promoter and other appropriate transcription regulatory elements, and transferred into prokaryotic or eukaryotic host cells to produce recombinant monkey cathepsin S protein. Techniques for such manipulations are fully described in Maniatis et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including E. coli, blue-green algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids, or viruses.

A variety of mammalian expression vectors may be used to express recombinant Canine Cathepsin S in mammalian cells. Commercially available mammalian expression vectors which may be suitable for recombinant Canine Cathepsin S expression, include but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUC-Tag (ATCC 37460), pEE12 (Cell Tech) and 1ZD35 (ATCC 37565).

A variety of bacterial expression vectors may be used to express recombinant Canine Cathepsin S in bacterial cells. Commercially available bacterial expression vectors that may be suitable for recombinant Canine Cathepsin S expression include, but are not limited to pET vectors (Novagen) and pQE vectors (Qiagen).

A variety of fungal cell expression vectors may be used to express recombinant Canine Cathepsin S in fungal cells such as yeast. Commercially available fungal cell expression vectors which may be suitable for recombinant Canine Cathepsin S expression include but are not limited to pYES2 (Invitrogen) and Pichia expression vector (Invitrogen).

A variety of insect cell expression vectors may be used to express recombinant Canine Cathepsin S in insect cells. Commercially available insect cell expression vectors which may be suitable for recombinant expression of Canine Cathepsin S include but are not limited to pBlueBacII (Invitrogen), pFastBac (GibcoBRL), pVL1392 (BD BioSciences), pAcUW51 (BD BioSciences), pVL1393 (BD BioSciences), and pAcHP2 (BD BioSciences).

DNA encoding monkey cathepsin S may be cloned into an expression vector for expression in a recombinant host cell. Recombinant host cells may be prokaryotic or eukaryotic, including but not limited to, bacteria such as E. coli, fungal cells such as yeast, mammalian cells including, but not limited to, cell lines of human, bovine, porcine, monkey and rodent origin, and insect cells including, but not limited to, drosophila and silkworm derived cell lines. Cell lines derived from mammalian species which may be suitable and which are commercially available include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including, but not limited to, transformation, transfection, protoplast fusion, lipofection, and electroporation. The expression vector-containing cells are clonally propagated and individually analyzed to determine whether they produce monkey cathepsin S protein. Identification of monkey cathepsin S expressing host cell clones may be done by several means including, but not limited to, immunological reactivity with anti-monkey cathepsin S antibodies, and the presence of host cell-associated monkey cathepsin S activity.

Expression of monkey cathepsin S DNA may also be performed using in vitro produced synthetic mRNA. Synthetic mRNA or mRNA isolated from monkey cathepsin S producing cells can be efficiently translated in various cell-free systems including, but not limited to, wheat germ extracts and reticulocyte extracts, as well as efficiently translated in cell based systems, including, but not limited to, microinjection into frog oocytes, with microinjection into frog oocytes being generally preferred.

To determine the monkey cathepsin S DNA sequence(s) that yields optimal levels of monkey cathepsin S activity and/or monkey cathepsin S protein, monkey cathepsin S DNA molecules including, but not limited to, the following can be constructed: the full-length open reading frame of the monkey cathepsin S cDNA encoding the 37 kDa protein from approximately base 73 to approximately base 1062 (these numbers correspond to first nucleotide of first methionine and last nucleotide before the first stop codon) and several constructs containing portions of the cDNA encoding monkey cathepsin S protein. All constructs can be designed to contain none, all or portions of the 5' or the 3' untranslated region of monkey cathepsin S cDNA. Monkey cathepsin S activity and levels of protein expression can be determined following the introduction, both singly and in combination, of these constructs into appropriate host cells. Following determination of the monkey cathepsin S DNA cassette yielding optimal expression in transient assays, this monkey cathepsin S DNA construct is transferred to a variety of expression vectors, for expression in host cells including, but not limited to, mammalian cells, baculovirus-infected insect cells, E. coli, and the yeast S. cerevisiae.

Assay Methods for Monkey Cathepsin S

Methods for detecting monkey cathepsin S activity may involve the direct measurement of monkey cathepsin S activity in whole cells transfected with monkey cathepsin S cDNA or oocytes injected with monkey cathepsin S mRNA. Monkey cathepsin S activity is measured by specific ligand binding or biological characteristics of the host cells expressing monkey cathepsin S DNA.

Cell Based Assays

The present invention provides a whole cell method to detect compound modulation of monkey cathepsin S. The method comprises the steps;

1) contacting a compound, and a cell that contains functional monkey cathepsin S, and 2) measuring a change in the cell in response to modified monkey cathepsin S function by the compound.

The amount of time necessary for cellular contact with the compound is empirically determined, for example, by running a time course with a known monkey cathepsin S modulator and measuring cellular changes as a function of time.

The measurement means of the method of the present invention can be further defined by comparing a cell that has been exposed to a compound to an identical cell that has not been similarly exposed to the compound. Alternatively two cells, one containing functional monkey cathepsin S and a second cell identical to the first, but lacking functional monkey cathepsin S, could be both be contacted with the same compound and compared for differences between the two cells. This technique is also useful in establishing the background noise of these assays. One of average skill in the art will appreciate that these control mechanisms also allow easy selection of cellular changes that are responsive to modulation of functional monkey cathepsin S.

The term "cell" refers to at least one cell, but includes a plurality of cells appropriate for the sensitivity of the detection method. Cells suitable for the present invention may be bacterial, yeast, or eukaryotic.

The assay methods to determine compound modulation of functional monkey cathepsin S can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The cellular changes suitable for the method of the present invention comprise directly measuring changes in the function or quantity of monkey cathepsin S, or by measuring downstream effects of monkey cathepsin S function, for example, by measuring secondary messenger concentrations or changes in transcription or by changes in protein levels of genes that are transcriptionally influenced by monkey cathepsin S, or by measuring phenotypic changes in the cell. Preferred measurement means include changes in the quantity of monkey cathepsin S protein, changes in the functional activity of monkey cathepsin S, changes in the quantity of mRNA, changes in intracellular protein, changes in cell surface protein, or secreted protein, or changes in Ca+2, cAMP or GTP concentration. Changes in the quantity or functional activity of monkey cathepsin S are described herein. Changes in the levels of mRNA are detected by reverse transcription polymerase chain reaction (RT-PCR) or by differential gene expression. Immunoaffinity, ligand affinity, or enzymatic measurement quantifies changes in levels of protein in host cells. Protein-specific affinity beads or specific antibodies are used to isolate for example $^{35}$S-methionine labeled or unlabelled protein. Labelled protein is analyzed by SDS-PAGE. Unlabelled protein is detected by Western blotting, cell surface detection by fluorescent cell sorting, cell image analysis, ELISA or RIA employing specific antibodies. Where the protein is an enzyme, the induction of protein is monitored by cleavage of a florigenic or colorimetric substrate.

A preferred detection means for secreted proteins that are enzymes such as proteases would be fluorescent or colorimetric enzymatic assays. Fluorescent/luminescent/color substrates for alkaline phosphatase are commercially available and such assays are easily adaptable to high throughput multi-well plate screen format. Fluorescent energy transfer based assays are used for protease assays. Fluorophore and quencher molecules are incorporated into the two ends of the peptide substrate of the protease. Upon cleavage of the specific substrate, separation of the fluorophore and quencher allows the fluorescence to be detectable. When the secreted protein could be measure by radioactive methods, scintillation proximity technology could be used. The substrate of the protein of interest is immobilized either by coating or incorporation on a solid support that contains a fluorescent material. A radioactive molecule, brought in close proximity to the solid phase by enzyme reaction, causes the fluorescent material to become excited and emit visible light. Emission of visible light forms the basis of detection of successful ligand/target interaction, and is measured by an appropriate monitoring device. An example of a scintillation proximity assay is disclosed in U.S. Pat. No. 4,568,649, issued Feb. 4, 1986. Materials for these types of assays are commercially available from Dupont NEN® (Boston, Mass.) under the trade name FlashPlate™.

A preferred detection means where the endogenous gene results in phenotypic cellular structural changes is statistical image analysis the cellular morphology or intracellular phenotypic changes. For example, but not by way of limitation, and cell may change morphology such a rounding versus remaining flat against a surface, or may become growth-surface independent and thus resemble transformed cell phenotype well known in the art of tumor cell biology, or a cell may produce new outgrowths. Phenotypic changes that may occur intracellularly include cytoskeletal changes, alteration in the entoplasmic reticulum/Golgi complex in response to new gene transcription, or production of new vesicles.

Where the endogenous gene encodes a soluble intracellular protein, changes in the endogenous gene may be measured by changes of the specific protein contained within the cell lysate. The soluble protein may be measured by the methods described herein.

The present invention is also directed to methods for screening for compounds that modulate the expression of DNA or RNA encoding monkey cathepsin S, as well as the function of monkey cathepsin S protein in vivo. Compounds may modulate by increasing or attenuating the expression of DNA or RNA encoding monkey cathepsin S, or the function of monkey cathepsin S protein. Compounds that modulate the expression of DNA or RNA encoding monkey cathepsin S or the function of monkey cathepsin S protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, and monkey cathepsin S.

Purification of Monkey Cathepsin S Protein

Following expression of monkey cathepsin S in a recombinant host cell, monkey cathepsin S protein may be recovered to provide purified monkey cathepsin S in active form. Several monkey cathepsin S purification procedures are available and suitable for use (Kirschke et al. (1986) Biochem. J. 240:455–459 Cathepsin S. The cysteine proteinase from bovine lymphoid tissue is distinct from cathepsin (Kopitar et al. (1996) Eur. J. Biochem). Folding and activation of human procathepsin S from inclusion bodies produced in *Escherichia coli*. Brömme et al. (1993) J. Biol. Chem. 268:4832–4838 Functional Expression of Human Cathepsin S in *Saccharomyces cerevisiae*. Brömme and McGrath (1996) Protein Science 5:789–791. High-level expression and crystallization of recombinant human cathepsin S). As described above for purification of monkey cathepsin S from natural sources, recombinant monkey cathepsin S may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography, lectin chromatography, antibody/ligand affinity chromatography or covalent chromatography using the reactive cysteine at the active site.

Recombinant monkey cathepsin S can be separated from other cellular proteins by use of an immunoaffinity column made with monoclonal or polyclonal antibodies specific for full-length nascent monkey cathepsin S, polypeptide fragments of monkey cathepsin S or monkey cathepsin S subunits. The affinity resin is then equilibrated in a suitable buffer, for example, phosphate buffered saline (pH 7.3), and the cell culture supernatants or cell extracts containing monkey cathepsin S or monkey cathepsin S subunits are slowly passed through the column. The column is then washed with the buffer until the optical density ($A_{280}$) falls to background, then the protein is eluted by changing the buffer condition, such as by lowering the pH using a buffer such as 0.23 M glycine-HCl (pH 2.6). The purified monkey cathepsin S protein is then dialyzed against a suitable buffer such as phosphate buffered saline.

Protein Based Assay

The present invention provides an in vitro protein assay method to detect compound modulation of monkey cathepsin S protein activity. The method comprises the steps;

1) contacting a compound, and function monkey cathepsin S protein, and
2) measuring a change to monkey cathepsin S function by the compound.

The amount of time necessary for cellular contact with the compound is empirically determined, for example, by running a time course with a known monkey cathepsin S modulator and measuring changes as a function of time.

Methods for detecting compounds that modulate monkey cathepsin S proteolytic activity comprise combining a punitive modulating compound, functional monkey cathepsin S protein, and a suitable labeled substrate and monitoring an effect of the compound on the protease by changes in the amount of substrate either as a function of time or after a predefined period of time. Labeled substrates include, but are not limited to; substrate that is radiolabeled (Coolican et al., *J. Biol. Chem.* (1986) 261:4170–76), fluorometric (Lonergan et al., *J. Food Sci.* (1995) 60:72–3, 78; Twining, *Anal. Biochem.* (1984) 143:30–34), or colorimetric (Buroker-Kilgore and Wang, *Anal. Biochem.* (1993) 208:387–92). Radioisotopes useful for use in the present invention include those well known in the art, specifically $^{125}I$, $^{131}I$, $^{3}H$, $^{14}C$, $^{35}S$, $^{32}P$, and $^{33}P$. Radioisotopes are introduced into the peptide by conventional means, such as iodination of a tyrosine residue, phosphorylation of a serine or threonine residue, or incorporation of tritium, carbon or sulfur utilizing radioactive amino acid precursors. Zymography following SDS polyacrylamide gel electrophoresis (Wadstroem and Smyth, *Sci. Tools* (1973) 20:17–21), as well as by fluorescent resonance energy transfer (FRET)-based methods (Ng and Auld, *Anal. Biochem.* (1989) 183:50–6) are also methods used to detect compounds that modulate monkey cathepsin S proteolytic activity. Compounds that are agonists will increase the rate of substrate degradation and will result in less remaining substrate as a function of time. Compounds that are antagonists will decrease the rate of substrate degradation and will result in greater remaining substrate as a function of time.

A preferred assay format useful for the method of the present invention is a FRET based method using peptide substrates that contain a fluorescent donor with either a quencher or acceptor that are separated by a peptide sequence encoding the monkey cathepsin S cleavage site. A fluorescent donor is a florigenic compound that can adsorb energy and transfers a portion of the energy to another compound. Examples of fluorescent donors suitable for use in the present invention include, but are not limited to, coumarins, xanthene dyes such as fluoresceins, rhodols, and rhodamines, resorufins, cyanine dyes bimanes, acridines, isoindols, dansyl dyes, aminophthalic hydrazides such as luminol and isoluminol derivatives, aminophthalimides, aminonapthalimides, aminobenzofurans, aminoquinolines, dicanohydroquinones, and europium and terbium complexes and related compounds. A quencher reduces the emission from the fluorescent donor when it is appropriately proximally located to the donor, and do not generally re-emit the energy in the form of fluorescence. Examples of such moieties include indigos, benzoquinones, anthraquinones, azo compounds, nitro compounds, indoanilines, and di- and triphenylmethanes. A FRET method using a donor/quencher pair measures increased emission from the fluorescent donor as a function of monkey cathepsin S enzymatic activity upon the peptide substrate. Therefore a test compound that antagonizes monkey cathepsin S will generate an emission signal between two control samples—a low (basal) fluorescence from the FRET peptide alone and a higher fluorescence from the FRET peptide digested by the activity of enzymatically active monkey cathepsin S. An acceptor is a fluorescent molecule that adsorbs energy from the fluorescent donor and re-emits a portion of the energy as fluorescence. An acceptor is a specific type of quencher that enables a separate mechanism to measure monkey cathepsin S proteolytic efficacy. Methods that utilize a donor/acceptor pair measure a decrease in acceptor emission as a function of monkey cathepsin S enzymatic activity upon the peptide substrate. Therefore a test compound that antagonizes monkey cathepsin S will generate an emission signal between two control samples—a higher basal fluorescence from the FRET peptide alone and a lower fluorescence from the FRET peptide digested by the activity of enzymatically active monkey cathepsin S. Examples of acceptor useful for methods of the present invention include, but are not limited to, coumarins, fluoresceins, rhodols, rhodamines, resorufins, cyanines, difuoroboradiazindacenes, and phthalcyanines.

Production and Use of Antibodies That Bind to Monkey Cathepsin S

Monospecific antibodies to monkey cathepsin S are purified from mammalian antisera containing antibodies reactive against monkey cathepsin S or are prepared as monoclonal antibodies reactive with monkey cathepsin S using the technique originally described by Kohler and Milstein, *Nature* (1975) 256:495–497. Immunological techniques are well known in the art and described in, for example, *Antibodies: A laboratory manual* published by Cold Spring Harbor Laboratory Press, Cold Spring Harbor, N.Y. (ISBN No. 0879693142). Monospecific antibody as used herein is defined as a single antibody species or multiple antibody species with homogenous binding characteristics for monkey cathepsin S. Homogenous binding as used herein refers to the ability of the antibody species to bind to a specific antigen or epitope, such as those associated with the monkey cathepsin S, as described above. Monkey cathepsin S specific antibodies are raised by immunizing animals such as mice, rats, guinea pigs, rabbits, goats, horses and the like, with rabbits being preferred, with an appropriate concentration of monkey cathepsin S either with or without an immune adjuvant.

Preimmune serum is collected prior to the first immunization. Each animal receives between about 0.001 mg and about 1000 mg of monkey cathepsin S associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of monkey cathepsin S in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. Approximately seven days after each booster immunization or about weekly after a single immunization, the animals are bled, the serum collected, and aliquots are stored at about −20° C.

Monoclonal antibodies (mAb) reactive with monkey cathepsin S are prepared by immunizing inbred mice, preferably Balb/c, with monkey cathepsin S. The mice are immunized by the IP or SC route with about 0.001 mg to about 1.0 mg, preferably about 0.1 mg, of monkey cathepsin S in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about two to thirty weeks. Immunized mice are given one or more booster immunizations of about 0.001 to about 1.0 mg of monkey cathepsin S in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 molecular weight, at concentrations from about 30% to 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about Days 14, 18, and 21 and are screened for antibody production by an immunoassay such as solid phase immunoradioassay (SPIRA) using monkey cathepsin S as the antigen. The culture fluids are also tested in the Ouchterlony precipitation assay to determine the isotype of the mAb. Hybridoma cells from antibody positive wells are cloned by a technique such as the soft agar technique of MacPherson, "Soft Agar Techniques", *Tissue Culture Methods and Applications* (Kruse and Paterson (Eds.) Academic Press, 1973, or by the technique of limited dilution.

Monoclonal antibodies are produced in vivo by injection of pristane primed Balb/c mice, approximately 0.5 ml per mouse, with about $1 \times 10^6$ to about $6 \times 10^6$ hybridoma cells at least four days after priming. Ascites fluid is collected at approximately eight to twelve days after cell transfer and the monoclonal antibodies are purified by techniques known in the art.

In vitro production of anti-monkey cathepsin S mAb carried out by growing the hybridoma in tissue culture media is well known in the art. High density in vitro cell culture may be conducted to produce large quantities of anti-monkey cathepsin S mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of monkey cathepsin S in body fluids or tissue and cell extracts.

It is readily apparent to those skilled in the art that the above described methods for producing monospecific antibodies may be utilized to produce antibodies specific for monkey cathepsin S polypeptide fragments, or full-length nascent monkey cathepsin S polypeptide, or the individual monkey cathepsin S subunits. Specifically, it is readily apparent to those skilled in the art that monospecific antibodies may be generated which are specific for only one monkey cathepsin S subunit or the fully functional monkey cathepsin S protein. It is also apparent to those skilled in the art that monospecific antibodies may be generated that inhibit normal function of monkey cathepsin S protein.

Monkey cathepsin S antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfhydryl groups on antibodies are well known in the art; amine groups are reactive with, for example, N-hydroxysuccinimide esters.

Since there is a significant difference in both the nucleic acid and amino acid sequences between the cathepsin S of different species, it is possible that inhibitors can be found that only inhibit a subset of the species. For treating human disease the inhibitors must work in humans. However, during the discovery and development of such compounds it is necessary to test these inhibitors in different animal models. In general it is best to know if a given inhibitor is active against the enzyme of that species. There are several Monkey models that could be used to test human cathepsin S inhibitors and therefore Monkey cathepsin S can be used determine if a given set of inhibitors can be used in these models. Once a compound is shown to be an inhibitor of human cathepsin S it can then be tested against Monkey cathepsin S before it is used in a Monkey model of human disease.

Kit Compositions Containing Monkey Cathepsin S Specific Reagents

Kits containing monkey cathepsin S DNA or RNA, antibodies to monkey cathepsin S, or monkey cathepsin S protein, may be prepared. Such kits are used to detect DNA that hybridizes to monkey cathepsin S DNA or to detect the presence of monkey cathepsin S protein or peptide fragments in a sample. Such characterization is useful for a variety of purposes including, but not limited to, forensic analyses, diagnostic applications, and epidemiological studies.

The DNA molecules, RNA molecules, recombinant protein and antibodies of the present invention may be used to screen and measure levels of monkey cathepsin S DNA, monkey cathepsin S RNA or monkey cathepsin S protein. The recombinant proteins, DNA molecules, RNA molecules and antibodies lend themselves to the formulation of kits suitable for the detection and typing of monkey cathepsin S. Such a kit would comprise a compartmentalized carrier suitable to hold in close confinement at least one container. The carrier would further comprise reagents such as recombinant monkey cathepsin S protein or anti-monkey cathepsin S antibodies suitable for detecting monkey cathepsin S. The carrier may also contain a means for detection such as labeled antigen or enzyme substrates or the like.

Gene Therapy

Nucleotide sequences that are complementary to the monkey cathepsin S encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other monkey cathepsin S antisense oligonucleotide mimetics. Monkey cathepsin S antisense molecules may be introduced into cells by microinjection, liposome encapsulation or by expression from vectors harboring the antisense sequence. Monkey cathepsin S antisense therapy may be particularly useful for the treatment of diseases where it is beneficial to reduce monkey cathepsin S activity.

Monkey cathepsin S gene therapy may be used to introduce monkey cathepsin S into the cells of target organisms. The monkey cathepsin S gene can be ligated into viral vectors that mediate transfer of the monkey cathepsin S DNA by infection of recipient host cells. Suitable viral vectors include retrovirus, adenovirus, adeno-associated virus, herpes virus, vaccinia virus, poliovirus and the like. Alternatively, monkey cathepsin S DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo monkey cathepsin S gene therapy. Monkey cathepsin S gene therapy may be particularly useful for the treatment of diseases where it is beneficial to elevate monkey cathepsin S activity. Protocols for molecular methodology of gene therapy suitable for use with the monkey cathepsin S gene is described in *Gene Therapy Protocols*, Paul D. Robbins (Ed.), (1996) Human Press, Totawa, N.J.

Pharmaceutical Compositions

Pharmaceutically useful compositions comprising monkey cathepsin S DNA, monkey cathepsin S RNA, or monkey cathepsin S protein, or modulators of monkey cathepsin S receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to a subject in amounts sufficient to treat or diagnose disorders in which modulation of cathepsin S-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the monkey cathepsin S receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of monkey cathepsin S can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a monkey cathepsin S modulating agent.

The daily dosage of the products may be varied over a wide range from 0.01 to 1,000 mg per patient, per day. For oral administration, the compositions are preferably provided in the form of scored or un-scored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the monkey cathepsin S receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methylcellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from approximately 0.005 to about 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Cloning of Monkey Cathepsin S cDNA

A Monkey SML B cell library was constructed from poly (A)+ selected RNA. Briefly, mRNA from $10 \times 10^6$ cells was purified on oligo(dT)-cellulose according to the manufacturers instructions (Invitrogen, San Diego, Calif.). 0.5 µg of mRNA was used to synthesize and amplify double-stranded cDNA (SMART cDNA synthesis kit, Clonetech, Palo Alto, Calif.). The resulting product was size-selected using a 0.8% low-melting agarose gel. cDNA in the range 0.6–5 kb was subsequently ligated into PCR 2.1 using TOPO TA cloning (Invitrogen, San Diego, Calif.) and transformed into *E. coli*.

A monkey cathepsin S probe was made from SML mRNA. Briefly, the product resulting from first strand synthesis was G-tailed using terminal transferase as described (ref). Nested primers derived from human cathepsin S were used together with a $C_{18}$ primer to amplify a 250 bp product by PCR. The resulting probe was labeled with $^{32}P$-dCTP by random priming (Stratagene, San Diego, Calif.) and used to screen the plated cDNA library. Library filters were prehybridized and hybridized according to standard protocols (buffer from Sigma). After hybridization the filters were washed twice at room temperature in 2× standard saline citrate (SSC)/0.2% SDS for fifteen minutes followed by two washes at 50° C. in 0.2×SSC/0.1% SDS for fifteen minutes. Filters were exposed to film and developed. DNA prepared from positive clones was subsequently sequenced using standard protocols and equipment (ABI 377, Perkin-Elmer, Norwalk, Conn.). Based on the full-length sequence, 5' (5'TATATAAGAATTCACCG CCATGAAGCAGCTGGTTTGTGTGCTGT3') SEQ ID NO: 3 and 3' (5'TATATAGTCGA CCTAGATTTCTGGGTAAGAGGG) SEQ ID NO: 4, primers were constructed, incorporating EcoRI and SalI sites respectively. These primers were used to amplify a full length PCR product from the SMART first strand product. After digestion with EcoRI and SalI the fragment was ligated into EcoRI- and SalI-digested pFastbac (GibcoBRL, Rockville, Md.).

EXAMPLE 2

Primary Structure of the Monkey Cathepsin S Protein

The nucleotide sequences of pmonkey cathepsin S revealed single large open reading frame of about monkey cathepsin S base pairs. The cDNAs have 5' and 3'-untranslated extensions of about 72 and about 78 nucleotides for pmonkey cathepsin S. The first in-frame methionine was designated as the initiation codon for an open reading frame that predicts a monkey cathepsin S protein with an estimated molecular mass ($M_r$) of about 37 kDa. The protein contained hydrophobic amino-terminal residues with sequences highly predictive of signal cleavage sites and a propeptide that is removed to result in predicted mature protein initiating at amino acid 115.

The predicted Monkey Cathepsin S protein was aligned with the Cathepsin S sequences from other species that are known (human, mouse, rat and bovine (mature protein only). There is an 95, 82 and 80% amino acid identity versus human, mouse and rat cathepsin S, respectively and 93, 72 and 74% conserved. When only the mature protein is considered the amino acid identities become 96, 88, 86 and 91% and 93, 81, 81 and 85% conserved versus human, mouse, rat and bovine. The monkey Cathepsin S sequence contains active site residues Cys at position 139, His at position 277 and Asn at position 297 which are conserved amongst all of the species whose sequence is known.

EXAMPLE 3

Cloning of the Monkey Cathepsin S cDNA into E. Coli Expression Vectors

Recombinant monkey cathepsin S is produced in *E. coli* following the transfer of the monkey cathepsin S expression cassette into *E. coli* expression vectors, including but not limited to, the pET series (Novagen). The pET vectors place monkey cathepsin S expression under control of the tightly regulated bacteriophage T7 promoter. Following transfer of this construct into an *E. coli* host that contains a chromosomal copy of the T7 RNA polymerase gene driven by the inducible lac promoter, expression of monkey cathepsin S is induced when an appropriate lac substrate (IPTG) is added to the culture. The levels of expressed monkey cathepsin S are determined by the assays described herein.

The cDNA encoding the entire open reading frame for monkey cathepsin S is inserted into the NdeI site of pET [16]11a. Constructs in the positive orientation are identified by sequence analysis and used to transform the expression host strain BL21. Transformants are then used to inoculate cultures for the production of monkey cathepsin S protein. Cultures may be grown in M9 or ZB media, whose formulation is known to those skilled in the art. After growth to an $OD_{600}=1.5$, expression of monkey cathepsin S is induced with 1 mM IPTG for three hours at 37° C.

EXAMPLE 4

Cloning of Monkey Cathepsin S cDNA into a Mammalian Expression Vector

The monkey cathepsin S cDNAs were cloned into the mammalian expression vectors pMAMneo and pcDNA3. The monkey cathepsin S Bluescript plasmids were digested with Not I and treated with Klenow enzyme to create a blunt cloning end. The inserts were excised with Sal I digestion and purified by agarose gel electrophoresis. The pMAMneo vector was treated with XhoI, Klenow enzyme and then SalI and calf intestinal phosphatase (CIP). The linear vector was purified on agarose gel and used to ligate to the monkey cathepsin S cDNA inserts. Recombinants were isolated, designated monkey cathepsin S, and used to transfect mammalian cells (L-cells) by $CaPO_4$-DNA precipitation. Stable cell clones were selected by growth in the presence of G418. Single G418 resistant clones were isolated and shown to contain the intact monkey cathepsin S gene. Clones containing the monkey cathepsin S cDNAs are analyzed for expression using immunological techniques, such as immunoprecipitation, Western blot, and immunofluorescence using antibodies specific to the monkey cathepsin S proteins. Antibody is obtained from rabbits inoculated with peptides that are synthesized from the amino acid sequence predicted from the monkey cathepsin S sequences.

The monkey cathepsin S genes were inserted into pcDNA3. Monkey cathepsin S was digested with XhoI and NotI and the cDNA inserts isolated by agarose gel electrophoresis. The vector, pcDNA3, was digested with XhoI and NotI, treated with CIP and the linear vector isolated by gel electrophoresis, and ligated with cDNA inserts. Recombinant plasmids monkey cathepsin S were used to transform the mammalian COS or CHO cells.

Cells that are expressing monkey cathepsin S, stably or transiently, are used to test for expression of the protease. These cells are used to identify and examine other compounds for their ability to modulate, inhibit or activate the protease and to compete for labeled substrate.

Cassettes containing the monkey cathepsin S cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL1651), and CV-1 tat [Sackevitz et al., *Science* (1987) 238:1575], 293, L (ATCC# CRL6362)] by standard methods including, but not limited to, electroporation, or chemical procedures (cationic liposomes, DEAE dextran, calcium phosphate). Transfected cells and cell culture supernatants can be harvested and analyzed for monkey cathepsin S expression as described herein.

All of the vectors used for mammalian transient expression can be used to establish stable cell lines expressing monkey cathepsin S. Unaltered monkey cathepsin S cDNA constructs cloned into expression vectors are expected to program host cells to make monkey cathepsin S protein. In addition, monkey cathepsin S is expressed extracellularly as a secreted protein by ligating monkey cathepsin S cDNA constructs to DNA encoding the signal sequence of a secreted protein. The transfection host cells include, but are not limited to, CV-1-P [Sackevitz et al., *Science* (1987) 238:1575], tk-L [Wigler et al., *Cell* (1977) 11:223], NS/0, and dHFr-CHO [Kaufman and Sharp, *J. Mol. Biol.* (1982) 159:601].

Co-transfection of any vector containing monkey cathepsin S cDNA with a drug selection plasmid including, but not limited to, G418, aminoglycoside phosphotransferase; hygromycin, hygromycin-B phosphotransferase; APRT, xanthine-guanine phosphoribosyl-transferase, will allow for the selection of stably transfected clones. Levels of monkey cathepsin S are quantitated by the assays described herein.

Monkey cathepsin S cDNA constructs are also ligated into vectors containing amplifiable drug-resistance markers for the production of mammalian cell clones synthesizing the highest possible levels of monkey cathepsin S. Following introduction of these constructs into cells, clones containing the plasmid are selected with the appropriate agent, and isolation of an over-expressing clone with a high copy number of plasmids is accomplished by selection in increasing doses of the agent.

The expression of recombinant monkey cathepsin S is achieved by transfection of full-length monkey cathepsin S cDNA into a mammalian host cell.

EXAMPLE 5

Cloning of Monkey Cathepsin S cDNA into a Baculovirus Expression Vector for Expression in Insect Cells Baculovirus vectors, which are derived from the genome of the AcNPV virus, are designed to provide high-level expression of cDNA in the Sf9 line of insect cells (ATCC CRL# 1711).

Expression of Monkey Cathepsin S cDNA

Sf9 insect cells and SFM II medium were purchased from GibcoBRL. Bacmids, Sf9 cell transfections and subsequent infections were made according to the manufacturers protocol (GibcoBRL). Primary and secondary virus stocks were allowed to totally lyse. Sf9 cells at 2.5–3×10$^6$ were infected at an MOI of 1 and allowed to totally lyse. Supernatants were removed and further processed. FIG. 3 shows the expression of the active protein from the cells.

EXAMPLE 6

Cloning of Monkey Cathepsin S cDNA into a Yeast Expression VECTOR

Recombinant monkey cathepsin S is produced in the yeast S. cerevisiae following the insertion of the optimal monkey cathepsin S cDNA cistron into expression vectors designed to direct the intracellular or extracellular expression of heterologous proteins. In the case of intracellular expression, vectors such as EmBLyex4 or the like are ligated to the monkey cathepsin S cistron [Rinas et al., Biotechnology (1990) 8:543–545; Horowitz et al., J. Biol. Chem. (1989) 265:4189–4192]. For extracellular expression, the monkey cathepsin S cistron is ligated into yeast expression vectors which fuse a secretion signal (a yeast or mammalian peptide) to the NH$_2$ terminus of the monkey cathepsin S protein [M. A. Jacobson, Gene (1989) 85:511–516); L. Riett and N. Bellon, Biochem. (1989) 28:2941–2949].

These vectors include, but are not limited to, pAVE1>6, which fuses the human serum albumin signal to the expressed cDNA [O. Steep, Biotechnology (1990) 8:42–46], and the vector pL8PL which fuses the human lysozyme signal to the expressed cDNA [Y. Yamamoto, Biochem. 28:2728–2732]. In addition, monkey cathepsin S is expressed in yeast as a fusion protein conjugated to ubiquitin utilizing the vector pVEP [D. J. Ecker, Biol. Chem. (1989) 264:7715–7719; E. A. Sabin, Biotechnology (1989) 7:705–709; D. P. McDonnell, Mol. Cell Biol. (1989) 9:5517–5523]. The levels of expressed monkey cathepsin S are determined by the assays described herein.

EXAMPLE 7

Purification of Recombinant Monkey Cathepsin S

Recombinantly produced monkey cathepsin S may be purified by antibody affinity chromatography.

Monkey cathepsin S antibody affinity columns are made by adding the anti-monkey cathepsin S antibodies to Affigel-10 (Biorad), a gel support that is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents, such as detergents, and the cell culture supernatants or cell extracts containing solubilized monkey cathepsin S are slowly passed through the column. The column is then washed with phosphate-buffered saline together with detergents until the optical density (A280) falls to background, then the protein is eluted with 0.23 M glycine-HCl (pH 2.6) together with detergents. The purified monkey cathepsin S protein is then dialyzed against 10 mM sodium acetate pH 4.5 buffer.

EXAMPLE 8

Purification of Recombinant Monkey Cathepsin S Using Thiopropyl Sepharose

Recombinantly produced Monkey Cathepsin S may be purified by thiopropyl Sepharose chromatography.

Monkey Cathepsin S was purified based on the published procedure for the purification of human cathepsin S [Vernet, 1993; McGrath, 1996]. In general, two liters of the supernatant from infected Sf9 cells was adjusted to pH 4.5 with 100 mM sodium acetate and incubated overnight at 4° C. Afterwards 7 grams of thiopropyl Sepharose 6B (Pharmacia, Uppsala, Sweden) was added and the solution was stirred overnight at 4° C. Washes and elutions were done in a batch mode and the filtrates were collected by filtration with a sintered glass filter. The Sepharose was washed two times with 250 mL of 100 mM sodium acetate pH 4.5, 1 mM EDTA and then two times with 250 mL of 100 mM Tris-HCl pH 8.0, 1 mM EDTA. The cathepsin S is then eluted by adding 100 mL of 100 mM MES pH 6.5 containing 1 mM EDTA, 10 mM DTT and 50 mM cysteine and stirring at room temperature for one hour. Elution is repeated three times to remove all of the bound cathepsin S. The activity is monitored using 20 μM Z-VVR-AMC as the substrate. The active fractions were pooled and dialyzed overnight against 10 mM sodium acetate pH 4.5 at 4° C. The dialyzed sample was adjusted to 25% glycerol and frozen at −80° C.

EXAMPLE 9

Assay for Inhibitors of Monkey Cathepsin S

Figure 4:
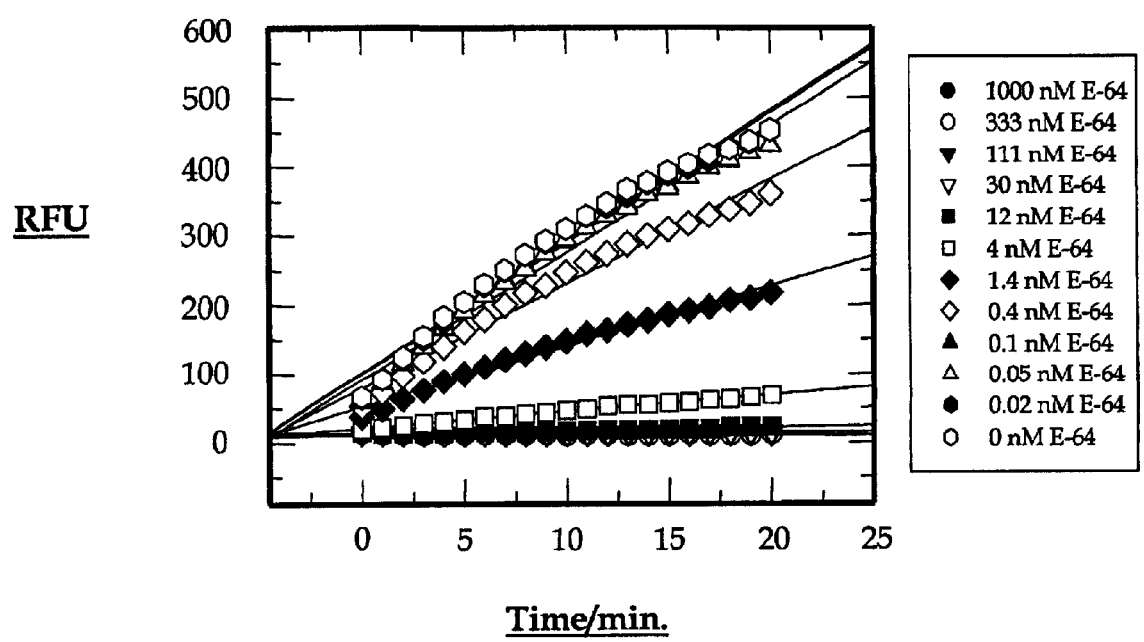
FIG. 4 Panels A and B: Modulation of monkey cathepsin S by a known monkey cathepsin S modulator is shown.

Inhibitors of Monkey Cathepsin S can be assayed using a fluorescent-based protease assay. All assays were carried out in a buffer consisting of 100 mM sodium acetate pH 5.0 containing 100 mM NaCl and 1.5 mM DTT. The substrate Z-VVR-AMC was used at a final concentration of 20 μM. The volume was 100 μL in a microtiter plate and the increase in fluorescence was read on a CytoFluor II (Perceptive Biosystems, Framingham, Mass.) using an excitation filter of 360/nm and an emission filter of 460/nm. The initial rate of product formation as judged by the increase in fluorescence intensity as a function of time was measured using linear regression. Inhibitors of Monkey cathepsin S lead to a decrease in this initial rate. The results are shown in FIG. 4.

What is claimed is:

1. An isolated and purified nucleic acid molecule comprising the nucleotide sequence set forth in SEQ ID NO: 1.

2. The nucleic acid molecule of claim 1 wherein the nucleic acid molecule is RNA.

3. The nucleic acid molecule of claim 1 wherein the nucleic acid molecule is DNA.

4. An expression vector comprising a nucleic acid sequence set forth in SEQ ID NO: 1.

5. A recombinant host cell comprising the expression vector of claim 4.

6. A substantially pure monkey Cathepsin S protease comprising the amino acid sequence set forth in SEQ ID NO:2.

7. A process for expression of monkey cathepsin S protein in a recombinant host cell, comprising:
   a) transferring the expression vector of claim 4 into suitable host cells; and
   b) culturing the host cells of step (a) under conditions which allow expression of the monkey cathepsin S protein from the expression vector.

8. A method of identifying compounds that inhibit monkey Cathepsin S protease activity, comprising:

a) combining a compound suspected of being an inhibitor of monkey Cathepsin S protease activity with the monkey Cathepsin S protease having the amino acid sequence set forth in SEQ ID NO:2; and b) measuring an effect of the compound on the protease activity of the monkey Cathepsin S protease, whereby an inhibitory compound is identified by a reduction in the protease activity of the monkey Cathepsin S protease.

* * * * *

SEQUENCE LISTING

<160> NUMBER OF SEQ ID NOS: 4

<210> SEQ ID NO 1
<211> LENGTH: 993
<212> TYPE: DNA
<213> ORGANISM: monkey

<400> SEQUENCE: 1

```
atgaagcagc tggtttgtgt gctgtttgtg tgctcctctg cggtgacaca gttgcataaa      60
gatcccaccc tggatcacca ctggaatctc tggaagaaaa cctacggcaa acaatataaa     120
gaaaagaatg aagaagcagt acgacgtctc atctgggaga agaatctaaa gtttgtgatg     180
cttcacaacc tggagcattc aatgggaatg cactcatatg atctgggcat gaaccacctg     240
ggagacatga ccagtgaaga agtgatgtct ttgatgagtt ccctgagagt tcccaaccag     300
tggcagagaa atatcacata taagtcaaac cctaatcaga tgttgcctga ttctgtggac     360
tggagagaaa agggtgtgt taccgaagtg aaatatcaag gttcttgtgg tgcttgctgg     420
gctttcagtg ctgtgggggc cctggaagca cagctgaagc tgaaaacagg aaagctggtg     480
tctctcagtg cccagaacct ggtggattgc tctgaaaaat atggaaacaa aggttgcaat     540
ggtggcttca tgacagaggc tttccagtac atcattgata acaaaggcat tgactcagaa     600
gcttcctatc cctacaaagc cacggatcag aaatgtcagt atgactcaaa atatcgtgct     660
gccacatgtt caaagtacac tgaacttccg tatggcagag aagatgtcct gaaagaagct     720
gtggccaata aggcccagt gtgtgttgga gtagatgcaa gtcatccttc cttcttcctc     780
tacagaagtg tgtctactaa tgacccagcc tgtactcaga aggtgaatca tggtgtactt     840
gtgattggct atggtgacct aatgggaaaa gaatactggc ttgtgaaaaa cagctggggc     900
agcaactttg gtgaacaagg atatattcgg atggcaagaa ataaaggaaa ccactgtggg     960
attgctagtt accctctta cccagaaatc tag                                   993
```

<210> SEQ ID NO 2
<211> LENGTH: 330
<212> TYPE: PRT
<213> ORGANISM: monkey

<400> SEQUENCE: 2

Met Lys Gln Leu Val Cys Val Leu Phe Val Cys Ser Ser Ala Val Thr
1               5                   10                  15

Gln Leu His Lys Asp Pro Thr Leu Asp His His Trp Asn Leu Trp Lys
            20                  25                  30

Lys Thr Tyr Gly Lys Gln Tyr Lys Glu Lys Asn Glu Glu Ala Val Arg
        35                  40                  45

Arg Leu Ile Trp Glu Lys Asn Leu Lys Phe Val Met Leu His Asn Leu
    50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Asn Gln Trp Gln Arg Asn Ile Thr Tyr Lys Ser Asn Pro Asn
            100                 105                 110

Gln Met Leu Pro Asp Ser Val Asp Trp Arg Glu Lys Gly Cys Val Thr
        115                 120                 125

Glu Val Lys Tyr Gln Gly Ser Cys Gly Ala Cys Trp Ala Phe Ser Ala

-continued

```
                130                 135                 140
Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Glu Lys Tyr Gly Asn
                165                 170                 175

Lys Gly Cys Asn Gly Gly Phe Met Thr Glu Ala Phe Gln Tyr Ile Ile
                180                 185                 190

Asp Asn Lys Gly Ile Asp Ser Glu Ala Ser Tyr Pro Tyr Lys Ala Thr
                195                 200                 205

Asp Gln Lys Cys Gln Tyr Asp Ser Lys Tyr Arg Ala Ala Thr Cys Ser
        210                 215                 220

Lys Tyr Thr Glu Leu Pro Tyr Gly Arg Glu Asp Val Leu Lys Glu Ala
225                 230                 235                 240

Val Ala Asn Lys Gly Pro Val Cys Val Gly Val Asp Ala Ser His Pro
                245                 250                 255

Ser Phe Phe Leu Tyr Arg Ser Gly Val Tyr Tyr Asp Pro Ala Cys Thr
                260                 265                 270

Gln Lys Val Asn His Gly Val Leu Val Ile Gly Tyr Gly Asp Leu Asn
                275                 280                 285

Gly Lys Glu Tyr Trp Leu Val Lys Asn Ser Trp Gly Ser Asn Phe Gly
        290                 295                 300

Glu Gln Gly Tyr Ile Arg Met Ala Arg Asn Lys Gly Asn His Cys Gly
305                 310                 315                 320

Ile Ala Ser Tyr Pro Ser Tyr Pro Glu Ile
                325                 330
```

<210> SEQ ID NO 3
<211> LENGTH: 44
<212> TYPE: DNA
<213> ORGANISM: Artificial Sequence
<220> FEATURE:
<223> OTHER INFORMATION: pcr primer

<400> SEQUENCE: 3
tatataagaa ttcaccgcca tgaagcagct ggtttgtgtg ctgt         44

<210> SEQ ID NO 4
<211> LENGTH: 33
<212> TYPE: DNA
<213> ORGANISM: Artificial Sequence
<220> FEATURE:
<223> OTHER INFORMATION: pcr primer

<400> SEQUENCE: 4
tatatagtcg acctagattt ctgggtaaga ggg         33